(12) United States Patent
Itoh et al.

(10) Patent No.: US 8,021,305 B2
(45) Date of Patent: Sep. 20, 2011

(54) ULTRASOUND PROBE, ULTRASONOGRAPH, AND ULTRASONOGRAPHY

(75) Inventors: Kouichi Itoh, Tokyo (JP); Tadashi Moriya, Kanagawa (JP); Takasuke Irie, Tokyo (JP)

(73) Assignee: Microsonic Co., Ltd., Tokyo (JP)

( * ) Notice: Subject to any disclaimer, the term of this patent is extended or adjusted under 35 U.S.C. 154(b) by 971 days.

(21) Appl. No.: 11/575,069

(22) PCT Filed: Sep. 12, 2005

(86) PCT No.: PCT/JP2005/016775
§ 371 (c)(1),
(2), (4) Date: Oct. 22, 2007

(87) PCT Pub. No.: WO2006/028249
PCT Pub. Date: Mar. 16, 2006

(65) Prior Publication Data
US 2008/0097217 A1  Apr. 24, 2008

(30) Foreign Application Priority Data
Sep. 10, 2004  (JP) ................................. 2004-264146

(51) Int. Cl.
*A61B 8/14* (2006.01)
(52) U.S. Cl. .................... 600/462; 600/459; 600/463
(58) Field of Classification Search .................. None
See application file for complete search history.

(56) References Cited

U.S. PATENT DOCUMENTS 5,284,148 A * 2/1994 Dias et al. ...................... 600/463
5,549,112 A   8/1996 Cockburn et al.
2003/0073904 A1 * 4/2003 Moriya et al. ................. 600/439

FOREIGN PATENT DOCUMENTS
EP  0672384  3/1995
(Continued)

OTHER PUBLICATIONS

Hu, Zhiqiang et al., "Katosei Denso Senro o Mochiita Pulse Asshuku Hoshiki Choonpa Naishikyo no Kento", The Transactions of the Institute of Electronics, Information and Communication Engineers A, Dec. 1, 2001, vol. J84-A, No. 12, pp. 1557-1564.

(Continued)

*Primary Examiner* — Unsu Jung
*Assistant Examiner* — Nigel Fontenot
(74) *Attorney, Agent, or Firm* — Lowe Hauptman Ham & Berner, LLP

(57) ABSTRACT

A non-invasive (having sufficiently small diameter so as not to give much pain to a subject) ultrasonic ultrasound probe of high spatial resolution and high signal-to-noise ratio, an ultrasonograph using the probe, and an ultrasonography are provided. The ultrasound probe is inserted into the tissue under examination and transmits an ultrasonic wave. The probe is characterized by comprising a hollow outer frame having one of needle shape, a puncture needle portion having the one end and inserted into the tissue of the subject, and an extended portion having the other end, an ultrasonic wave generating source positioned in the hollow part of the extended portion and generating an ultrasonic wave, an acoustic waveguide disposed along the length direction in the hollow part of the outer frame, capable of ultrasonic vibration, and adapted to transmit an ultrasonic wave, and direction changing means for changing the direction of the ultrasonic wave beam transmitted by the acoustic waveguide to the direction toward the position of the tissue under examination.

15 Claims, 5 Drawing Sheets

FOREIGN PATENT DOCUMENTS

| | | |
|---|---|---|
| JP | 2107238 | 4/1990 |
| JP | 2107239 | 4/1990 |
| JP | 8-47497 | 2/1996 |
| JP | 8047497 | 2/1996 |
| JP | 8-154936 | 6/1996 |
| JP | 8-154936 A | 6/1996 |
| JP | 8154936 | 6/1996 |
| JP | 11206759 | 8/1999 |
| JP | 2001198127 | 7/2001 |

OTHER PUBLICATIONS

Tsuyoshi Kochi et al. "Katosei Denso Senro o Mochiita Pulse Asshuku Hoshiki Choonpa Naishikyo no Kento", The Transactions of the Institute of Electronics, Information and Communication Engineers A, Dec. 1, 2001, vol. J84-A, No. 12, pp. 1557-1564.

* cited by examiner

ULTRASOUND PROBE, ULTRASONOGRAPH, AND ULTRASONOGRAPHY

RELATED APPLICATIONS

The present application is based on International Application No. PCT/JP2005/016775, filed on Sep. 12, 2005, which in turn corresponds to Japanese Application No. 2004-264146 filed on Sep. 10, 2004, and priority is hereby claimed under 35 U.S.C. §119 based on these applications. Each of these applications are hereby incorporated by reference in their entirety into the present application.

TECHNICAL FIELD

The present invention relates to an ultrasound probe for use in diagnostic ultrasonic imaging and relates especially to a probe that is inserted into body tissue to obtain its images, to an ultrasonograph, and to ultrasonography.

BACKGROUND OF THE INVENTION

The ultrasonograph has been used as a non-invasive, X-ray radiation free, and more convenient diagnostic tool than X-ray, CT (Computed Tomography), or MRI (Magnetic Resonance Imaging). Although CT and MRI provide images of high quality, they take up much space and are more expensive. Also, X-ray examination is invasive because of its X-ray radiation.

The ultrasonograph is said to provide images of low quality because its depth of penetration decreases with increase in frequency of an ultrasonic wave used to obtain of high resolution. For example, an ultrasonic wave with a frequency of 3 to 10 MHz is used in the conventional ultrasonic imaging system. In this case, depth of penetration is approximately 3 to 15 cm. It is difficult to obtain a sufficient resolution in the order of some 10 microns using an ultrasonic wave of such low frequency.

To obtain a high resolution in the order of 10 microns, it is necessary to use an ultrasonic wave with a frequency greater than 100 MHz; however, depth of penetration at this high frequency is less than approximately 1 mm, making it impossible to obtain images of deep tissue using conventional ultrasonic imaging systems.

Accordingly, to diagnose diseases with high accuracy, it is necessary to use such high frequency and to place the probe close to the region of interest. Therefore, an intraductal system capable, for example, of transesophageal scanning, in which the probe is inserted through the esophagus; or intravascular ultrasound (IVUS), in which the probe is inserted through a vessel, is employed.

The transesophageal approach, in particular, transesophageal echocardiography (TEE) is suited for examining organs to which the transcutaneous ultrasonic wave is not applicable because of interference of the ribs and lungs. On the other hand, intravascular ultrasound (IVUS) is a medical imaging methodology using a thin probe inserted into a blood vessel to diagnose the tissue. Examination by TEE is conducted by inserting a rotary probe placed at the tip of an endoscope into the esophagus for transmitting and receiving the ultrasonic wave. IVUS is performed by inserting a thin catheter for transmitting and receiving an ultrasonic wave into the vessel, but it is invasive and requires extra caution when electricity is used in the body.

Conclusion: these modalities have lost convenience and non-invasiveness.

Generally speaking, because established diagnosis is not obtained by ultrasonic imaging alone, ultrasonic imaging is carried out after CT or MRI examination. To make a definite diagnosis of the tissue, a specimen is obtained by biopsy under ultrasonic wave guidance and is processed for microscopic evaluation. This procedure is considered reliable for establishing a diagnosis, and enjoys widespread use; however, the results may require several days. Surgery therefore can not be carried out, even when abnormal findings are reported by the examination, until the established diagnosis is obtained. Further, because pathological examination of the resected slice obtained under laparotomy can not be carried out immediately, a follow-up operation is required. Laparotomy is sometimes interrupted until the pathological diagnosis is established, placing severe stress on the patient, who is kept waiting with an open abdominal incision.

To obtain an accurate diagnosis, an ultrasonic apparatus for the industrial use is tried for the medical use. The apparatus operates in the range of tens to hundreds of megahertz, a considerably higher frequency range than that of conventional ultrasonographs, in which several megahertz to tens of megahertz is used.

A focusing device is used in ultrasonic microscopy to focus the ultrasound beam. Because ultrasonic microscopy allows a pathologic diagnosis of the undyed specimen, results are available sooner than with optical microscopic methods, which require a dyed specimen. Ultrasonic microscopy has been considered for medical diagnosis, for which biopsy is performed to acquire the specimen, which is located on the path of the ultrasound beam. Because of the complexity of the procedure, this method is used only for the limited case in which time is a critical consideration.

A puncture needle-type ultrasonography was developed as an ultrasonic method to facilitate tissue diagnosis based on B-mode images [Japanese Unexamined Patent Application Nos. H02-107238 (reference 1), and H02-107239 (reference 2)]. In these apparatuses, an ultrasound probe is placed inside an outer hollow needle, and the needle is inserted into body tissue. The probe can be placed close to the region of interest, and can acquire images of high quality from deeply situated tissue using high-frequency ultrasound.

According to references 1 and 2, however, the puncture needle itself is a probe, and the ultrasound transducer is placed in the needle, necessarily increasing the diameter of the needle. The needle is 3 to 4 mm in diameter even when a small transducer is used. Use of a needle of such large diameter for puncture places the patient under a heavy burden and loses the advantage of non-invasiveness.

Accordingly, the transducer must be small enough to be mounted in the probe. However, a smaller transducer transmits less ultrasonic energy, and the resulting poor signal-to-noise ratio (S/N) precludes imaging deep tissues. Producing adequate ultrasonic energy with a small transducer requires high voltage, which demands extra caution for patient safety and sacrifices the convenience of the procedure.

Japanese Unexamined Patent Application No. H11-206759 describes a small needle-type ultrasound probe and an ultrasonic microscope. The apparatus uses an ultrasound beam of high frequency, around 100 MHz, and is used to diagnose the tissue by inserting the probe into body tissue. Because the probe is in the form of a needle, it is about 5 mm in diameter. Reducing its diameter to less than 1 mm in diameter would be difficult, yet it would still be too large to insert into body tissue and lose non-invasiveness completely. Further, because the probe is inserted into body tissue, strict safety measures would have to be followed.

As previously pointed out, a needle-type ultrasonic microscope, in which an ultrasound transducer is installed, suffers the disadvantages of being both invasive and difficult to use with assured safety.

On the other hand, an intraductal ultrasonic device [Japanese Unexamined Patent Application No. 2001-198127] and an ultrasonic treatment device [Japanese Unexamined Patent Application No. 2002-153483] both use fused quartz fibers. In these devices, the ultrasonic wave is transmitted along a fused quartz fiber. They differ intrinsically from the present invention, which operates as an ultrasonic microscope using, preferably, a fiber. The inventions described above have the drawbacks in non-invasiveness, and they do not improve a spatial resolution (of the images), because they use the low-frequency ultrasonic waves and do not enable the operator to control minutely the position of the tip of the fiber.

Japanese Unexamined Patent Application No. 2003-116898 discloses an ultrasonograph and an ultrasonic applicator for therapy. The objective of this invention is to transmit a high-intensity ultrasound beam using fused quartz fibers placed inside the ductal organ to the tip of the fiber to treat the region of interest: bladder stones, for example.

Here, a bundle of fibers transmits a high-power ultrasound beam. Further, according to reference 6, an ultrasound beam with a frequency as low as 1 MHz was used. The invention covered by reference 6 differs completely from the present invention, which enables the operator to obtain imaging at the cell level, showing the actual cell structure.

The invention disclosed by reference 6 has the drawbacks of not being non-invasiveness and of having low spatial resolution.

Reference 1: Japan Unexamined Patent Application No. H02-107238 (A11)
Reference 2: Japan Unexamined Patent Application No. H02-1072389 (A11)
Reference 3: Japan Unexamined Patent Application No. H11-206759 (A11)
Reference 4: Japan Unexamined Patent Application No. 2001-198127 (A11)
Reference 5: Japan Unexamined Patent Application No. 2002-153483 (A11)
Reference 6: Japan Unexamined Patent Application No. 2003-116869 (A11)

DISCLOSURE OF THE INVENTION

Problems to be Solved by the Invention

The main objective of this invention is to provide a high-resolution ultrasonograph and ultrasonography while maintaining such features of ultrasonic diagnosis as non-invasiveness and convenience.

Another objective of this invention is to provide an ultrasound probe that has an outer diameter so small that can it be inserted into body tissue without placing a severe burden on the patient and still retain non-invasiveness.

Means for Solving the Problems

As shown by claim 1, the probe invented to satisfy said objectives is an ultrasound probe for insertion into body tissue and that transmits ultrasonic waves, comprises:

(a) a hollow outer frame with a needle tip in the distal-end region consisted of a needle portion including said distal-end region for insertion into body tissue and an extended region portion at the other end;

(b) an ultrasound generator (transducer) placed in the bore of said extended portion, generating said ultrasonic wave;

(c) an acoustic waveguide located in the bore of said outer frame, said acoustic waveguide transmitting said ultrasonic wave and being movable in the axial direction;

(d) an ultrasound beam deflection device placed in the bore of said puncture needle portion to change the direction of the ultrasound beam transmitted via said acoustic waveguide to the direction of the tissue under examination.

The invention according to claim 2 comprises an ultrasound probe wherein said acoustic waveguide is manufactured so that it is in the bore of outer frame and is attachable to and/or removable from said puncture needle portion along the axial direction.

The invention according to claim 3 is an ultrasound probe comprising an inner tube in said bore of said outer frame extending from said needle portion to said extended portion so that said inner tube can be moved within a certain distance along the axis, and at least said acoustic waveguide and said ultrasound beam deflection device being housed within said inner tube.

The invention according to claim 4 is an ultrasound probe wherein said ultrasound beam deflection device is capable of focusing an ultrasound beam transmitted along said acoustic waveguide.

The invention according to claim 5 is an ultrasound probe wherein an acoustic window for the transmission of the ultrasonic wave deflected by said ultrasound beam deflection device is installed at a part of said outer frame, or at a part of said outer frame and said inner tube, and said acoustic window at a part of said outer frame comes in contact with said tissue under examination.

The invention according to claim 6 is an ultrasound probe comprising at least part of said acoustic waveguide and is composed of sapphire or fused quartz.

The invention according to claim 7 is an ultrasound probe wherein a higher mode of the Pocchamer-Chree wave is used as an ultrasonic wave.

The invention according to claim 8 is an ultrasound probe wherein at least a part of said acoustic waveguide is composed of material with an attenuation constant for an ultrasound beam ultrasonic wave that is intrinsically equal to or less than that of sapphire or fused quartz over the frequency range of 100 to 200 MHz.

The invention according to claim 9, wherein said ultrasound beam deflection device is placed perpendicular to the direction of the ultrasonic wave transmitted from said acoustic waveguide, and includes a mirror with a plane or curved surface is installed placed at a certain angle to said direction.

The invention according to claim 10 is an ultrasound probe wherein said ultrasound beam deflection device with a plane or curved surface is constructed on the end face of said acoustic waveguide.

The invention according to claim 11 is an ultrasound probe wherein said ultrasound beam deflection device is composed of the first mirror with a plane or curved surface positioned facing in the direction of the ultrasound beam that is transmitted from the side of said acoustic waveguide, and the second mirror with a plane or curved surface that reflects the ultrasonic wave reflected by the first mirror.

The invention according to claim 12 is an ultrasound probe wherein the diameter of the part of said probe inserted into body tissue is less than 1 mm.

The invention according to claim 13 is an ultrasonograph using an ultrasound probe that can be inserted into body tissue, comprising:
(a) said probe according to one of claims 1, and 4 to 12; and
(b) an ultrasound transmitting/receiving means wherein an ultrasonic wave transmitted via said acoustic waveguide and said ultrasound beam deflection device to the tissue under examination, and the ultrasonic wave reflected by said tissue and received via said ultrasound beam deflection device and said acoustic waveguide are controlled separately.

The invention according to 14 is an ultrasonograph using an ultrasound probe inserted into body tissue comprising:
(a) said ultrasound probe according to one of claims 2, 3, and 4 to 12;
(b) a position-controlling means wherein the transmitting position of an ultrasound beam transmitted to the tissue from said ultrasound probe is controlled by changing the position of said acoustic waveguide within said region; and
(c) an ultrasound transmitting/receiving means wherein an ultrasonic wave is transmitted via said acoustic waveguide and said ultrasound beam deflection device to the tissue under examination, and the ultrasound beam reflected by said tissue is received via said ultrasound beam deflection device and said acoustic waveguide.

The invention according to claim 15 is an ultrasonography using the ultrasonograph according claim 13 comprising:
(a) a step to insert said ultrasound probe into or close to the tissue under examination;
(b) a step to transmit an ultrasound beam to the tissue under examination via said acoustic waveguide and said ultrasound beam deflection device;
(c) a step to receive the ultrasonic wave reflected by the tissue under examination via said ultrasound beam deflection device and said acoustic waveguide; and
(d) a step to analyze the received signal wherein the transmitted signal is separated from the received signal.

The invention according to claim 16 is an ultrasonography using the ultrasonograph according claim 14 comprising:
(a) a step to insert said ultrasonic probe into or close to the tissue under examination;
(b) a step to transmit the ultrasound beam to the tissue under examination via said acoustic waveguide and said ultrasound beam deflection device;
(c) a step to receive the ultrasonic wave reflected by the tissue under examination via said ultrasound beam deflection device and said acoustic waveguide;
(d) the position of transmitting the ultrasound beam is controlled to scan the tissue under examination by using said position-controlling means; and
(e) a step to analyze the received signal wherein the transmitted signal is separated from the received signal.

The ultrasound probe according to claim 1 is equipped with an ultrasound transducer that transmits an ultrasonic wave at the end (the first end), an ultrasound beam deflection device that changes the direction of propagation of the ultrasonic wave (the second end), an acoustic waveguide connecting acoustically between the transducer and the ultrasound beam deflection device, and an outer frame that contains the ultrasound beam deflection device, the acoustic waveguide, and the transducer.

The outer frame is composed of a puncture needle portion and an extended portion, and at least a part of the acoustic waveguide and the ultrasound beam deflection device is installed inside the puncture needle portion that is in the form of a needle at the second part and capable of being inserted into body tissue and coming in contact with the tissue under examination The rest of the acoustic waveguide and the transducer are installed inside the extended portion of the outer structure including the first part.

Accordingly, the acoustic waveguide can be moved axially inside the outer frame, and the ultrasonic wave excited by the transducer can be transmitted to the ultrasound beam deflection device.

A favorable feature regarding the ultrasonic probe according to claim 2 is that the acoustic waveguide is replaceable with respect to the outer frame, including the puncture needle portion in the bore of the outer frame.

Specifically, the puncture needle portion and the extended portion of the outer frame are connected by a connection part, and the extended portion of the outer frame is unified with the ultrasound transducer and the acoustic waveguide attached to the ultrasound transducer.

A favorable feature regarding the ultrasound probe according to claim 3 is that an inner tube is placed in the bore through the extended portion and the puncture needle portion of the outer frame, the inner tube being movable within a certain length along the axis with respect to the said puncture needle portion.

The acoustic waveguide and the ultrasound beam deflection device are placed in the inner tube.

Specifically, the inner tube is equipped with a tubular extended portion, and the ultrasound transducer attached to the acoustic waveguide is placed inside the tubular extended portion. The tubular extended portion of the inner tube is mounted on a scanning mechanism, and the positions of all parts in the inner tube, including the ultrasound transducer, the acoustic waveguide, and the ultrasound beam deflection device, are changed by the scanning device controller, which comprises the scanning device and the scanning device controller.

In this way, the scanning across the tissue is accomplished by shifting the transmitting position of the ultrasonic beam by moving the ultrasound beam deflection device within a limited range without moving the puncture needle inserted into the body tissue.

Further, the puncture needle portion and the extended portion of the outer frame are connected by the connection part. Accordingly, the expanded part of the outer frame is unified with the inner tube inside via the scanning mechanism. Therefore, the inner tube is attached or removed from the puncture needle portion by inserting the inner tube in the bore of the puncture needle portion and by connecting the extended portion and the connection part of the puncture needle portion using the reverse procedure.

An optical device such as a mirror or a prism can be used as the ultrasound beam deflection device where the curvature of these devices can be altered to change the direction and to focus the ultrasound beam.

Preferably the acoustic waveguide and the ultrasound beam deflection device are connected in order to guide the ultrasonic wave in the body tissue.

The acoustic waveguide should be made thin and flexible by using materials like optical fiber made of fused quartz.

Preferably the outer frame will have an acoustic window to radiate the ultrasonic wave deflected by the ultrasound beam deflection device to the tissue under examination.

The function of the invented the ultrasound probe is to transmit the ultrasonic wave generated by the transducer to the ultrasound beam deflection device (such as a mirror) via the acoustic waveguide (composed, for example, of acoustic fiber), where the ultrasonic wave is deflected, focused, and radiated through the acoustic window to the tissue under examination.

If the inner tube and scanning device are installed, the inner tube including, the fiber, can be made to reciprocate, and the region of interest is scanned by ultrasound beam.

Preferably, the ultrasonic wave reflected by the tissue is transmitted through the acoustic window, deflected by the ultrasound deflection device, to the transducer via the acoustic waveguide, and then an image of the tissue is obtained using the detected signal.

The ultrasound probe is usually disposed of immediately after use because it has been inserted into and come in contact with body tissue. However, if the puncture needle portion and the extended portion is connected by the connection part in the outer frame, the ultrasound probe can be disassembled and the puncture needle portion alone can be discarded.

The optimum frequency range for this invention is 50 MHz to 1 GHz. Preferably, the puncture needle will be less than 800 microns in diameter.

The fiber can be made from sapphire, fused quartz, or diamond.

The acoustic waveguide can be made of any materials that have low attenuation constants for ultrasonic waves comparable to those of sapphire at frequencies greater than 100 MHz.

The inventor's research indicates that the physical and acoustical properties of sapphire make it the material of choice for this device.

EFFECT OF THE INVENTION

Because the ultrasound transducer is housed in the extended portion of the outer frame and is separate from the needle portion that is inserted into body tissue, a large transducer can be installed, the diameter of the transducer being unrelated to that of the puncture needle portion.

Accordingly, the probe can be constructed with the diameter of the needle portion small enough to maintain non-invasiveness, and, at the same time, with a diameter sufficient to obtain adequate penetration depth with a high-frequency ultrasonic wave.

According to claim 2, because the acoustic waveguide is manufactured so that it attached or removed along the axial direction, at least the extended portion including the acoustic waveguide can be used repeatedly by removing the puncture needle portion after use.

According to claim 3, the ultrasound beam deflecting device can be moved a limited distance along the axis through the inner tube in which the ultrasound beam deflecting device is housed, enabling ultrasonic scanning of the tissue without moving the needle portion inserted into the tissue.

Further, because the inner tube can be attached to or detached from the puncture needle portion, said acoustic waveguide, said ultrasound beam deflecting device, and the inner tube in which said acoustic waveguide and said ultrasound beam deflecting device are housed can be used repeatedly by removing the puncture needle portion after use.

The present invention provides an ultrasonograph, maintaining the convenience of the conventional ultrasonograph, and obtaining high-resolution ultrasonic images in real time. This invention supports real-time pathologic diagnosis of tissue from high-resolution images depicting cell-level tissue structure.

The present invention enables the physician to diagnose tissue using a transducer with a large diameter placed outside the body and a puncture needle of very small diameter inserted into body tissue.

Further, this invention can radiate a high-frequency ultrasonic wave from the beam deflecting device placed close to the tissue and obtain a high-resolution ultrasonic image.

The large transducer can obtain high-resolution images with a high signal-to-noise ratio in deep tissues.

With the present invention, the diameter of the puncture needle can be less than 1 mm, the ideal diameter of the puncture needle being less than 800 microns. This maintains non-invasiveness even when the puncture needle is inserted transcutaneously, because the accompanying level of pain is minimal.

Figure 1:
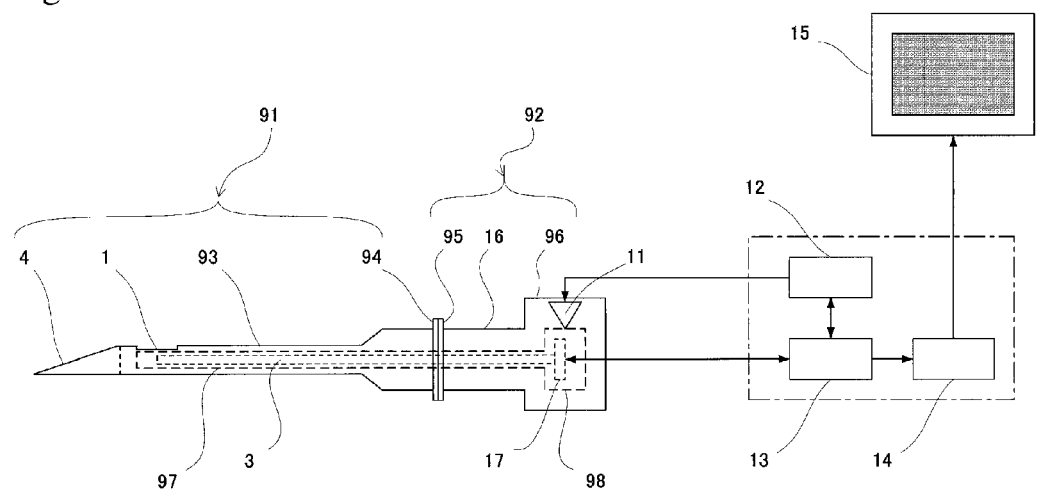
FIG. 1 Diagrammatic representation of the first ultrasonograph according to example 1.

DESCRIPTION OF THE REFERENCE NUMERALS 1, 1a Acoustic window
2 Mirror (an ultrasound beam deflection device used as to control the direction of the beam)
31 First mirror (ultrasound beam deflection device)
32 Second mirror (ultrasound beam deflection device)
3 Fiber (acoustic waveguide)
3a Tip of the fiber
4 Tip of the puncture needle
5, 5a Acoustic medium
6 Ultrasound matching layer
11 Scanning device
12 Scanning device controller
13 Transmitter/Receiver
14 Image processor
15 Monitor
16 Connecting tube (extended portion of outer frame)
17 Transducer (ultrasound generator)
18 Transducer element (ultrasound generator)
20,22 Acoustic lens
42,43 Waterproofing ring
44 Holder
91 Puncture needle portion (of the outer frame of the ultrasound probe)
92 Extended portion (of the outer frame of the ultrasound probe)
93 Outer frame (of the puncture needle portion)

93a Inner wall (of the outer frame)
94 Connection part (of the puncture needle portion)
95 Connection part (of the extended portion)
96 Expanded part (of the extended portion)
97 Inner tube
97a Inner wall (of the inner tube)
98 Expanded part (of the inner tube)

DETAILED DESCRIPTION OF THE INVENTION

A preferred embodiment of the invention is explained below with reference to the drawings.

Example 1

FIG. 1 shows the overall structure of the invented needle-type ultrasonograph.

FIG. 1 shows that the outer frame of the ultrasound probe is a hollow tube with a puncture needle portion (91) on one end and an extended portion (92) on its other end.

The puncture needle portion (91) is the part of the outer frame that is inserted into body tissue and is consisted of a hollow outer frame (93) with the sharpened tip (4) at the other end.

The extended portion (92) is equipped with an extended part (96) at one end; and the puncture needle portion (91) and the extended portion (92) are joined by connectors (94, 95).

The inner diameter of the extended part (96) of the extended portion (92) is larger than that of the outer frame (93) of the puncture needle portion (91).

The hollow inner tube (97) is placed inside the outer frame through the puncture needle portion (91) and the extended portion (92). The expanded part (98) of the inner tube is housed inside the extended part (96) of the extended portion (92) of the outer frame, and is connected to the scanning device (11).

The fiber (acoustic waveguide) (3) is installed inside the inner tube (97), and ultrasonic wave excited by the transducer (ultrasound generator) (17) housed in the expanded part (98) of the inner tube (97) is transmitted to the tip of said fiber (3).

It is possible to fabricate a portion of the acoustic waveguide 3 housed in the extended portion (92) and that of the part housed inside the puncture needle portion using the same or different materials for both.

The acoustic waveguide (3) can be made with core material (not shown), and its clad material (not shown).

In either case, because neither the transducer (17) nor the portion of the fiber contained inside the extended portion (92) are inserted into body tissue, this portion can be large.

The connecting tube (16) of the extended portion (92) connecting the expanded part (96) and the connecting portion (95) can be flexible.

As previously described, the expanded part (98) of the inner tube (97) is attached to the scanning device (11) which enables it to reciprocate the inner tube (97) containing the fiber (3).

The scanning device (11) causes, as described below, the transducer (17) and, accordingly, the tip of the fiber (3), to reciprocate the scanning ultrasonic wave radiated from the acoustic window (1) formed close to the tip of the outer frame (93) of the puncture needle portion (91).

Here, the scanning device controller (12) controls the scan of the ultrasound beam by the scanning device (11); the transmitter/receiver (13) radiates and receives the ultrasonic waves excited by the transducer (17).

The previously mentioned ultrasonic wave radiated to the body tissue from the puncture needle portion is reflected from the body tissue, containing its sonographic signal, and is sent to the transmitter/receiver (13) through the acoustic waveguide (5). The information is then processed by the imaging section (14) and displayed on the monitor (15).

The puncture needle portion (91) is attached to the extended portion (92) of the outer frame by connectors (94, 95). The extended portion (92) containing the scanning device (11), the transducer (17) and fiber (3) installed inside the inner tube (97) is separated from the needle portion (91) by disassembling after the probe has been inserted into body tissue.

Because it comes in contact with body tissue, the puncture needle portion (91) must be disposable to prevent infection.

On the other hand, because the extended portion (92) and the parts installed inside it, as well as the portions in the bore of the puncture needle need not be discarded, the expanded part can be used repeatedly to reduce cost.

However, all these parts, along with the puncture needle (91) and the extended portion (92), must be discarded if the acoustic window (1) is broken.

Example 2

Figure 2:
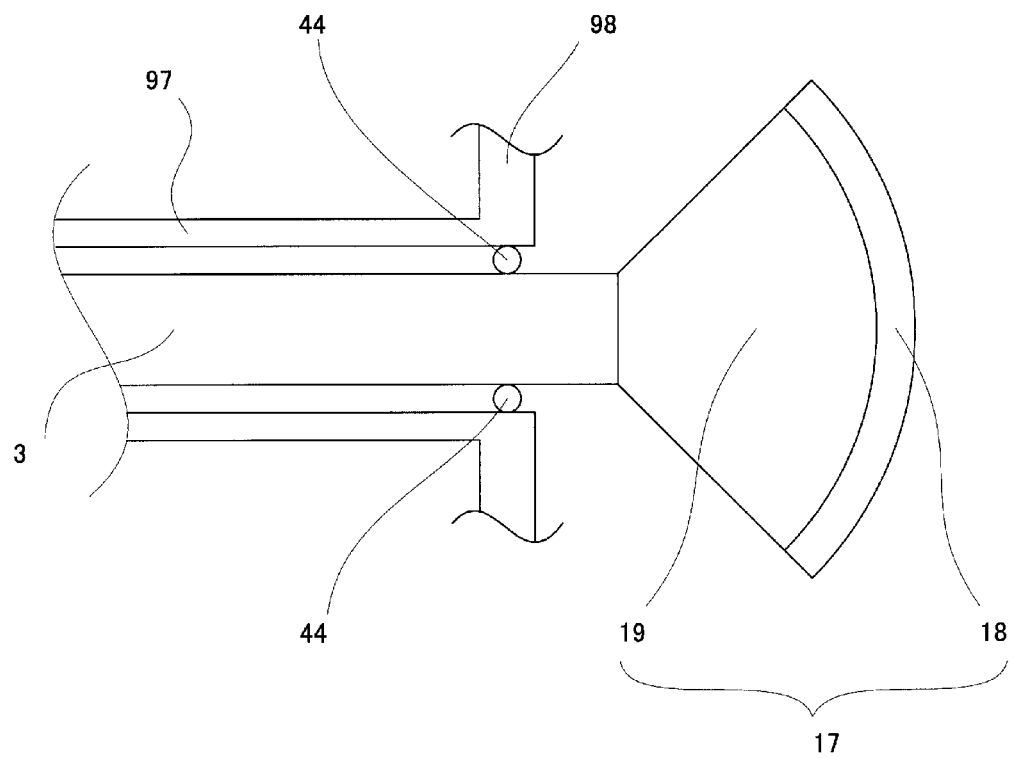
FIG. 2 First embodiment of the transducer of the ultrasound probe according to Example 2 of the invention.

FIG. 2 is a schematic embodiment of the transducer (17). The transducer element (18) generates an ultrasonic wave.

According to the design of the invention, because the transducer is placed outside the body, an ultrasound transducer 1 to 30 mm in diameter can be used, thus providing much more power.

The transducer element (18) is attached to the fiber (3).

FIG. 2 shows that the fiber (3) can be extended to the position where the transducer (17) is connected, and the transducer element (17) and the fiber (3) are connected by the acoustic medium (19), which is made of the same material as that of the fiber (3).

Regarding the fiber (3) as shown FIG. 2, a thin sapphire or fused quartz fiber can be used as an acoustic waveguide.

In FIG. 2, ultrasonic waves converge on the end face of the fiber (3) using a concave transducer (18), transmitting a large amount of ultrasonic energy to the fiber (3) via the acoustic medium (19)

The acoustic medium (19) can consist of the same material as the fiber (3) or any material with the similar acoustic properties.

A holder (44) is placed between the inner tube (97) and the fiber (3), maintaining the gap, and suppressing the attenuation of the ultrasonic wave resulting from penetration into the inner tube.

The holders can be placed in any of several places along the axis in the gap between the inner tube (97) and the fiber (3).

The holder is fixed, for example, by a recess whose cross section appears semicircular when formed on the surface of the inner tube (not shown), which is usually used.

The holder (44) is used to hold the fiber (3) against the wall of the inner tube (97) without attenuating the ultrasonic wave propagating along the fiber (3). When the fiber (3) touches the inner wall, low friction is required: preferably, it is made from a ring with a circular cross section or several spheres (ball bearings).

Example 3

Figure 3:
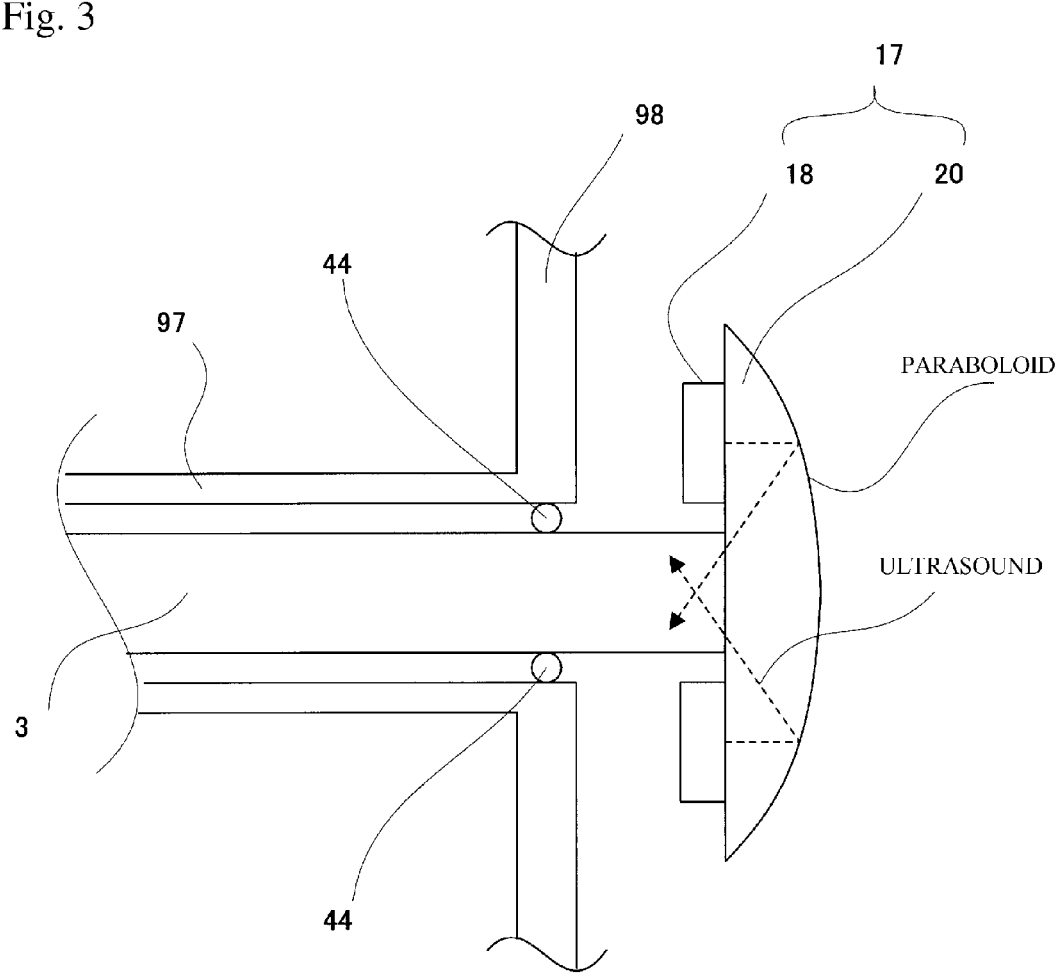
FIG. 3 Second embodiment of the transducer of the ultrasound probe according to Example 3 according to the invention.

FIG. 3 is a schematic representation of the second embodiment of the ultrasound transducer (17).

In FIG. 3, the ultrasonic waves transmitted by a disk-shaped transducer element (18) with a hole through its center converge after passing through an acoustic lens (20) of large diameter on the surface of the end of the fiber (3), producing a large quantity of ultrasonic energy.

The acoustic lens (20) can consist of the same material as the fiber or of any other material with similar acoustic properties.

Example 4

Figure 8:
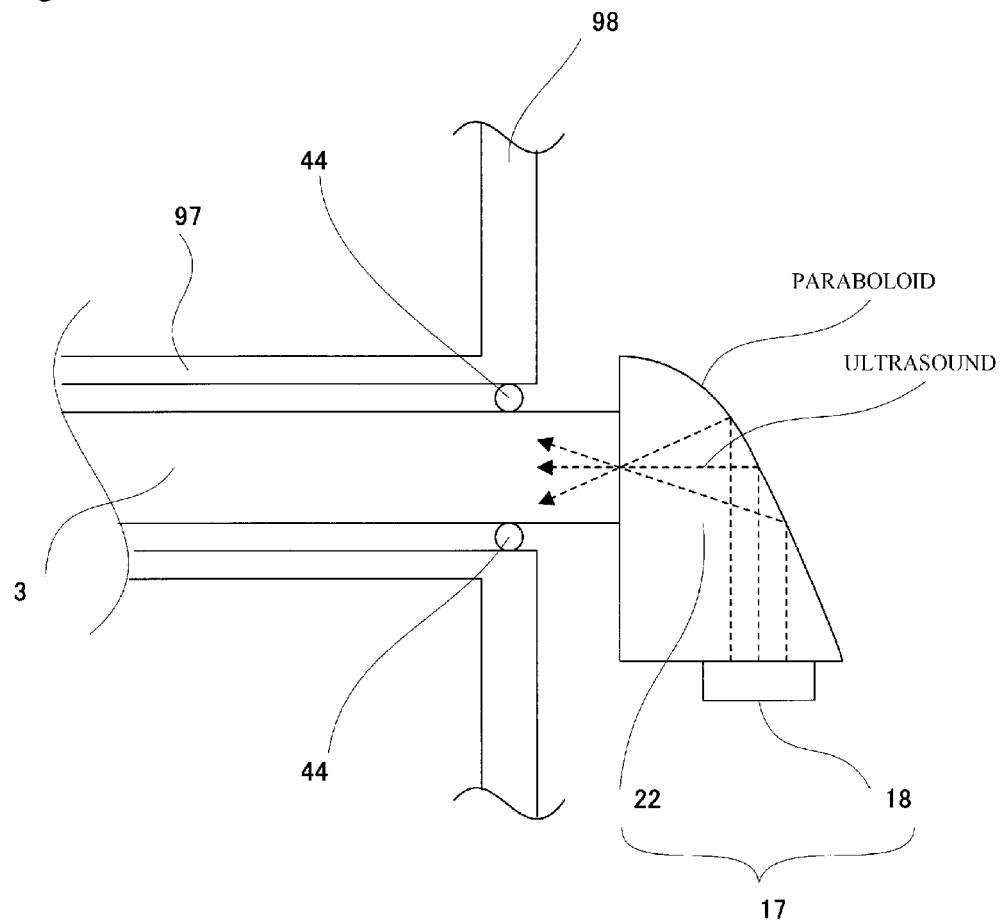
FIG. 8 Third embodiment of the transducer of the ultrasonograph according to Example 4 of the invention.

FIG. 8 is a schematic representation of the third embodiment of the ultrasound transducer (17).

In FIG. 8, ultrasonic waves excited by a disk-shaped transducer of large diameter converge at the acoustic lens (22) with a parabolic surface part of a paraboloid at the end of the fiber (3), transmitting to it a large amount of ultrasonic energy.

In this case, the shape of the ultrasound transducer is simpler than that shown in Example 3.

The lens (22) can consist of the same material as that of the fiber or of any material with the same or similar acoustic properties.

In this invention, because the ultrasonic wave is generated by a transducer (17) located outside the body and is transmitted into body tissue via the fiber (3), the diameter of the transducer can be large.

To transmit the ultrasonic waves generated by a large transducer into the fiber (3) efficiently, a method to guide and focus the ultrasonic waves into the end terminal surface of the fiber (3) is necessary.

In FIG. 2, the acoustic medium (19) placed between the transducer element (18) and the fiber (3), preferably made of the same materials as those of the fiber (3), plays a role in the method.

In FIG. 3, an acoustic lens (20) with a parabolic surface part of a paraboloid, preferably made of the same materials as the fiber (3) and placed opposite the transducer element (18), provides the essence of the method.

In FIG. 8, an acoustic lens (22) with a paraboloid surface and preferably made of the same material as the fiber (3), and that is placed opposite the disk-shaped transducer (18) provides the essence of the method.

However, the embodiments shown in FIGS. 2, 3, and 8 are examples, and any embodiment employing a method of exciting an ultrasonic wave with a high level of energy and focusing the ultrasonic wave on the end face of the fiber is sufficient.

The ultrasonic (radiation) energy can be expressed as $W=(P^2 \cdot S)/(\rho \cdot c)$, where W is acoustic pressure, S is the area of the transducer, $\rho$ is the density of the medium, and c is the propagation velocity.

When the needle-type ultrasonograph described above is used, a small transducer, one preferably less than 1 mm in diameter, is used to avoid causing the patient unnecessary pain.

On the other hand, because a large transducer 1 to 30 mm in diameter placed outside the body, as this invention makes possible, can be used, 1 to 900 times more ultrasound energy is made available because area is proportional to the square of the diameter.

Further, because the ultrasound waves converge at the acoustic lens, much of the ultrasonic energy is transmitted via the fiber.

When the ultrasonic wave is propagated along the fiber, conversion efficiency varies with the acoustic properties of the materials and the diameter of the fiber at any given frequency.

Conversion efficiency $\eta$ is defined as the ratio of input energy to output energy when a plane wave is transmitted through the fiber.

As is generally known, the L(0,1), L(02), and L(0,3) modes of the longitudinal wave of the Pocchammer-Chree wave propagate in the fiber.

Figure 7:
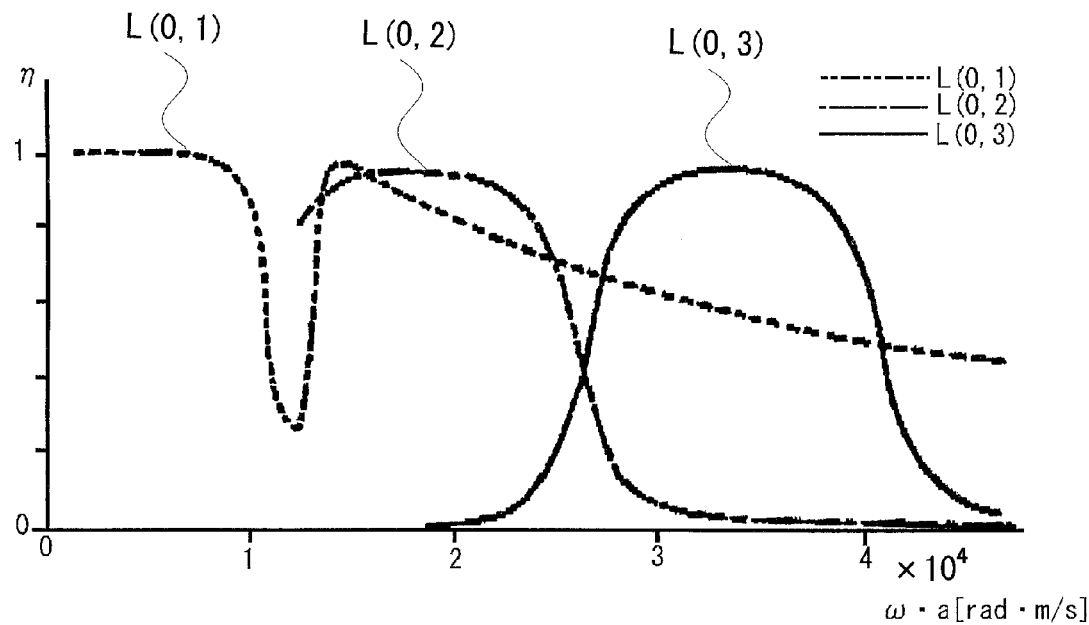
FIG. 7 Deflection efficiency curve for the $L(0,1)$, $L(0,2)$, and $L(0,3)$ modes of the Pocchammer-Chree wave as a function of $\omega a$ where $\omega$ is an angular frequency and a is the radius of the fiber.

The conversion efficiencies of these modes depend upon $\omega \cdot a$, where $\omega$ is angular frequency and a is the radius of the fiber, as shown in FIG. 7.

According to FIG. 7, the L(0,3) mode has a higher conversion efficiency, $\eta$, at a higher frequency. The higher modes are therefore preferable in this embodiment. Otherwise, the diameter of the fiber becomes so small that it prevents propagation of a high-energy ultrasonic wave.

According to the relation previously described, it is possible to determine the frequency of the ultrasonic wave and the diameter of the fiber.

For example, the preferable frequency of the embodiment is greater than 100 MHz, and there is no upper limit of propagation; however, the higher ultrasound frequency used, the thinner the fiber must be because of the relation between $\eta$ and $\omega \cdot a$. Therefore, in this case higher modes such as L(0,4) and L(0,5), which have no industrial application, can be used.

Fiber diameter should be determined taking into account the relation between the conversion efficiency $\eta$ and the frequency f, the allowable diameter of the ultrasound probe related to non-invasiveness.

For example, the radius of the fiber ranges from 20 to 80 microns; however, 30 to 40 microns at 150 MHz is preferable. In this case, the value would be $\omega \cdot a \approx 2\pi \cdot 150 \cdot 10^6 \cdot (30-40) \cdot 10^{-6} = (2.8-3.8) \cdot 10^4$, a value corresponding to the L(0,3) mode.

Next, the mechanism that radiates an ultrasonic wave generated by the transducer element (18) to the body from the tip of the puncture needle via the fiber (3) is disclosed. The ultrasound probe of the invented puncture needle-type ultrasonograph is inserted into body tissue, and radiates an ultrasonic wave close to the target tissue.

Example 5

Figure 4:
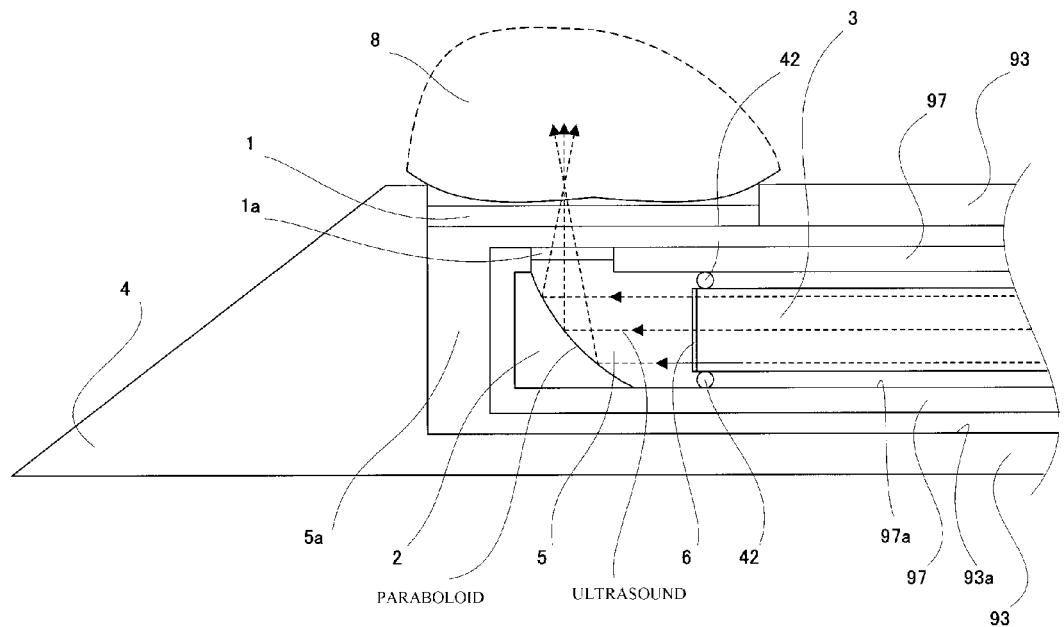
FIG. 4 First embodiment of the puncture needle portion (91) of the ultrasound probe according to example 5 of the invention.

FIG. 4 shows the first embodiment of the needle portion (91) of the invented puncture needle-type ultrasonograph.

The needle portion (91) comprises an outer frame (93) with the sharpened tip of the puncture needle (4) at its end. An inner tube (97) is installed inside the outer frame, and the fiber (3) serves as an acoustic waveguide transmitting an ultrasonic wave generated by an ultrasound_transducer (17).

The tip_of the puncture needle (4) is sharpened to allow it to be easily inserted into body tissue. The diameter of the needle is preferably is less than 1 mm, preferably much less than 800 microns.

A mirror (2) with a part of paraboloidal surface, revolutionary paraboidal surface, or a similar surface is installed at the tip of the inner tube (97), and the ultrasound wave generated by the transducer being transmitted via the fiber is radiated radially from the mirror (usually in the direction of the axis of the ultrasound probe). The mirror, used as an ultrasound beam deflection device, not only changes the direction of the ultrasound beam, but increases the energy density radiated to body tissue, enhancing spatial resolution, especially through its focusing effect, and the lateral resolution of the image.

The space between the fiber (3) and the ultrasound beam deflection device (2) is filled with an acoustic medium (5) such as distilled water to enhance transmission efficiency.

The space in the bore of the outer frame (93) near the tip of the puncture needle (4) is filled with the acoustic medium (5a). When the inner tube (97) is inserted into the bore of the outer frame, some of the acoustic medium (5a) moves into the space between the inner wall (93a) of the outer frame and the side wall of the inner tube (97).

An ultrasound matching layer (6) is formed between the fiber (3) and the acoustic medium (5), the acoustic impedance of the layer being the square root of those of the fiber and the acoustic medium, and the thickness being either one-quarter wavelength or multiple wavelengths plus one-quarter wavelength [(λ/4), or (λ/4)+nλ] of the layer to enhance the transmission efficiency of the ultrasonic wave.

The ultrasound probe has an acoustic window (1) near its tip that is formed by cutting away part of the outer frame (93).

The inner tube has an acoustic window (1a) smaller than the acoustic window (1) formed by cutting away part of the tip of the inner tube (97), the window being removed when the acoustic medium (5) and (5a) are made of the same material.

These acoustic windows (1, 1a) are thin layers of the material, usually organic substances, that conduct the ultrasonic wave efficiently.

The acoustic window allows the ultrasound beam to insonate the tissue efficiently, while, at the same time, avoiding contact with such parts as the inner tube (97) including the fiber (3) that are not disposable with the tissue under examination (8).

The ultrasound beam transmitted radially by the mirror (2), which serves as an ultrasound beam deflection device, is radiated to the tissue under examination (8) via the acoustic window (1).

Ultrasound wave beam scanning is thus performed through said acoustic window. Scanning is carried out by imparting a reciprocating motion to the inner tube (97) in which the transducer (17) to which the fiber (3) is attached in the outer frame by the scanning device (11). Specifically, one of the acoustic windows (1a) reciprocates relative to the other acoustic window (1), traveling a distance of 50 to 200 microns in each direction.

Preferably, therefore, the acoustic window (1) should be rectangular, elliptical, or polygonal, and its length should be 500 to 1000 microns.

The mirror (2) exemplifies the embodiment of the ultrasound beam deflection device. The mirror (2) radiates the ultrasound beam conducted by the fiber (3) through the acoustic window (1a, 1), focusing the ultrasound beam and changing the direction of propagation as necessary. The ultrasonic wave reflected by the tissue, the echo, is focused on the end face of the fiber (3), and detected by the transducer (17). Preferably, the fiber (3) will be made of sapphire or fused quartz, and the diameter of the outer frame will be less than 1 mm. However, the diameter can be greater as long as non-invasiveness is maintained. If, for example, the ultrasonic diagnosis is made while the patient is anesthetized, the outer diameter can exceed 1 mm. In such a case, the advantage of this invention, namely, that the diagnosis of the tissue under examination (8) is carried out in real time, is maintained.

The acoustic medium (5), water or saline with approximately the same acoustic impedance as body tissue, conducts the ultrasonic wave back and forth between the fiber (3) and the acoustic window.

The space between the tip of the fiber (3) and the inner wall (97a) of the inner tube is made watertight by a waterproofing ring (42) that does not interfere with the ultrasonic vibration along the axis but prevents penetration of the acoustic medium (5) into said space.

The inner tube (97) is inserted into the outer frame (93) of the puncture needle portion (91), and the position of the inner tube (97) containing the transducer (17), the fiber (3) attached to the transducer (17), the acoustic medium (5), and the mirror (2) are minutely moved within the outer frame by the scanning device. In this way, ultrasound beam scanning is performed through the acoustic window (1).

Example 6

Figure 9:
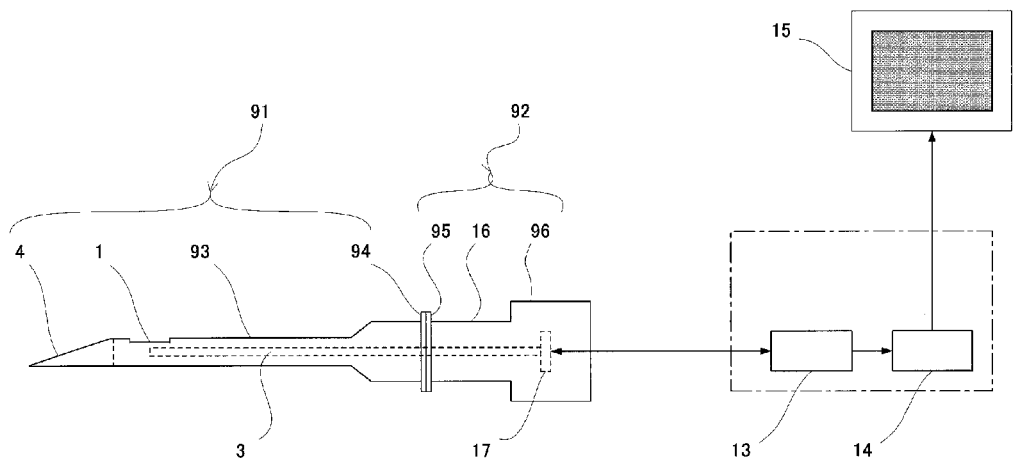
FIG. 9 Diagrammatic representation of the second ultrasonograph according to Example 6 of the invention.

FIG. 9 shows the second embodiment of the invented ultrasonograph, which differs from that described in Example 1, the inner tube (97) having been removed, the fiber (3) having been placed inside the bore of the outer frame, and the ultrasound beam deflection device, mirror (2), having been attached to the tip of the bore of the outer frame (93) of the puncture needle portion (91) (not shown).

Accordingly, the beam is transmitted in a fixed direction, and scanning is not performed. Because, the inner tube has been eliminated, the outer diameter of the outer frame (93) of the puncture needle portion (91) can be smaller and the diameter of the fiber can be larger than those represented in Example 1, or the manufacturing tolerances of the diameters can be greater.

This embodiment can be used for A-mode or M-mode presentation.

Example 7

Figure 5:
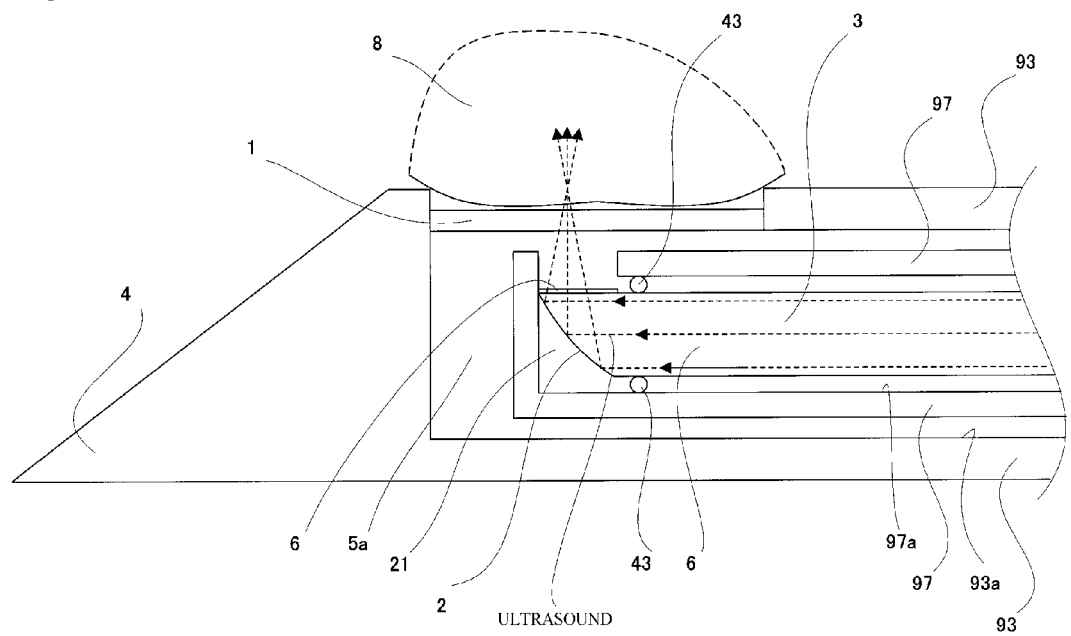
FIG. 5 Second example of the puncture needle portion (91) of the ultrasound probe according to Example 7 of the invention.

The second embodiment of the puncture needle portion (91) of the ultrasound probe is shown in FIG. 5.

In this embodiment, focusing and ultrasonic beam deflection are performed by a part of a paraboloidal surface formed at the tip of the fiber which functions as a mirrors as well as a focusing device to focus the ultrasonic beam and deflecting mirror to transmit the ultrasound beam to the tissue through the acoustic window changing the direction, which is different from the said Example 5.

Accordingly, in this embodiment, the part of a paraboloidal surface at the tip of the fiber functions as an ultrasound beam deflection device (2).

The acoustic window (1) is placed between the tissue under examination (8) and the acoustic medium (5a), being made from a waterproofing layer that transmits the ultrasonic wave and has acoustic properties (such as the acoustic impedance) similar to those of the acoustic medium (5a).

In this embodiment, preferably the tip of the fiber in the form of the part of a paraboloidal surface, for example, is in contact with air (21). Differing from Example 4 (FIG. 4), although the acoustic medium (5) is not necessary, waterproofing is necessary in order to prevent reflux of the acoustic medium (5a) into the space between the outer frame (93) and the inner tube, and a waterproofing ring (43) that does not interfere with the axial ultrasonic vibration is installed to prevent penetration of the acoustic medium (5a) into the space between the fiber (3) and the inner wall (97a) of the inner tube.

The ultrasound beam deflection device in this embodiment transmits the ultrasonic wave ultrasound beam by contacting and by fixing the ultrasound matching layer (6) to the acoustic window (1), because the inner tube (97) and the acoustic medium (5a) are removed.

Ultrasonic scanning of the tissue also can be accomplished by reducing the friction between the matching layer (6) and the acoustic window (1), filling the interface with the acoustic medium (oil or jelly, for example), and using a reciprocating fiber which is installed on the scanning device.

Example 8

Figure 6:
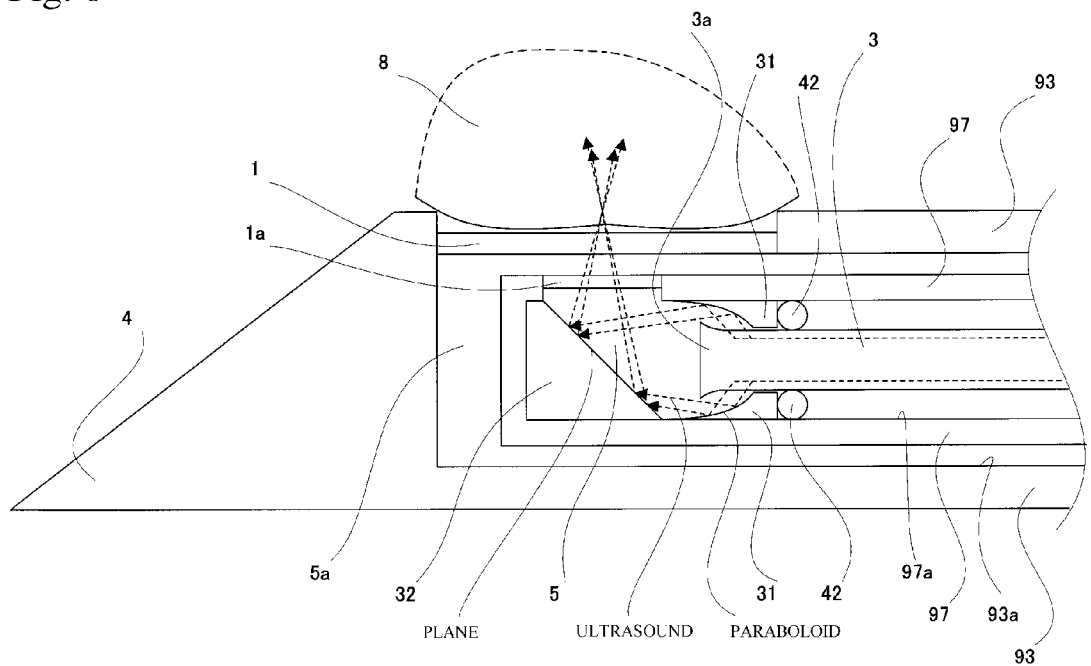
FIG. 6 Third example of the puncture needle portion (91) of the ultrasound probe according to Example 8 of the invention.

FIG. 6 shows the third embodiment of the needle portion (91) of the invented ultrasound probe. According to this embodiment, the ultrasonic wave can be transmitted to the acoustic medium (5) from the fiber (3) without using the acoustic matching layer, as is also the case in Examples 5 and 7. In this embodiment, the diameter increases exponentially as it approaches the tip, increasing the amplitude of the surface wave. Thus the ultrasonic wave is transmitted from the side of the fiber, deflected and directed obliquely by a reflection device such as the first mirror (31), which is placed between the fiber (3) and the inner wall (97a) of the inner tube (97).

The mirror is placed in the acoustic medium (5).

In this embodiment, the inner surface of the mirror (31) is a part of a paraboloid centered by the tip of the fiber (3). The ultrasonic wave radiated by the surface wave propagating on the surface of the fiber, is radiated obliquely with respect to the axis of the fiber, and is directed to the axis of the fiber (3) by the mirror (31).

The ultrasonic wave directed to the axis of the fiber (3) is reflected by the second plane mirror (32) placed opposite the tip of the fiber, and is radiated to the tissue under examination (8) through the acoustic window (1).

A plane mirror (32) is placed at a 45 degree angle to the axis of the fiber.

In this embodiment, as in Example 5, the inner tube (97) is installed, and the fiber (3), the acoustic medium (5), and two mirrors (31, 32), are housed in and fixed to the inner tube (97). (However, the fiber (3) is not in acoustic contact with the wall of the inner tube (97).

Thus, as in Example 5, the puncture needle portion (91) of the outer frame can be discarded. On the other hand, the extended portion (92) of the housing as well as the inner tube (97) and expensive parts contained therein are all reusable.

The parameters of the paraboloidal mirror (31) and the positions and the directions in which the mirrors (31, 32) are aimed are determined so that the ultrasound beams reflected by the mirrors is focused on the region of interest in the tissue under examination (8).

The embodiment is featured by the use of the surface wave that transmits the ultrasonic wave obliquely from the surface of the fiber (3), being focused by the mirror, and the radiation of the ultrasonic wave to the region of interest, removing the use of the ultrasound matching layer, and decreasing ultrasonic propagation loss.

The invented puncture needle-type ultrasonograph can be used to examine the abdomen (liver, kidney, pancreas, gall bladder, spleen, stomach wall, walls of the intestines, and the like), soft tissue (breast, thyroid gland, mammary gland, joints, tendons, and the like) from the surface of the body.

Another use of this invention would be to use the puncture needle to examine tissues through the dissecting window during open surgery.

In either case, diagnostic ultrasound systems are commonly used by placing the probe on the surface of the body or directly on an internal organ during surgery to examine tissues and to guide the surgeon to the proper location.

The invention relates to the ultrasonograph in that the puncture needle is inserted into body tissue, transmitting/receiving the ultrasonic signals using the ultrasound transmitter/receiver and the ultrasound transducer, transmitting the ultrasonic wave along the fiber, focusing and directing it on tissue via the acoustic window. The ultrasonic wave reflected from the tissue is reflected back to the ultrasound transmitter/receiver via the acoustic window, and the received ultrasonic signal is then analyzed, converted into a video signal, and displayed on a monitor.

The present invention provides a B-mode image of the tissue. The B-mode image, in turn, provides the resolution at the cellular level. Images with cellular-level resolution make it possible to distinguish between malignant tissue such as cancer, and normal tissue.

The invention provides Doppler mode image (Color/Power Doppler), M-mode presentation (to indicate ventricular motion of the heart).

The invention can also be used to take measurements in A-mode, the fundamental mode of the ultrasonograph.

INDUSTRIAL APPLICABILITY

The invented puncture needle-type ultrasonograph is suited, for example, for examination by insertion of the puncture needle following the general inspection such as the detection of the region of interest using the conventional ultrasonograph.

According to the invention, because the use of a high-frequency and a high-power ultrasonic wave is possible, high resolution images in the depth direction are obtained and able to provide information in cell-size detail.

The fiber is usually 20 to 150 microns in diameter. The diameter of the puncture needle that holds the fiber, usually about 800 microns, is easily tolerated by the patient.

According to the ultrasound diagnostic method embodied in this invention, diagnosis and pathologic examination planning for treatment can be carried out immediately on completion of the ultrasonic examination.

In addition, because microscopic-image information is obtained by inserting the puncture needle into the organ directly from the incision during surgery, the operation can continue without interruption with the information provided by the image.

What is claimed is:

1. An ultrasound probe adapted to be inserted into body tissue for transmitting ultrasonic waves, said ultrasound probe comprising:
   a hollow outer frame having (i) a needle portion at a distal end region and (ii) an extended portion at the other end region opposite to the distal end region, said needle portion being adapted to be inserted into the body tissue,
   an ultrasound transducer placed in a bore of said outer frame at said extended portion;
   an acoustic waveguide located in the bore of said outer frame, said acoustic waveguide being movable in an axial direction of the probe and configured to transmit said ultrasonic wave; and
   an ultrasound beam deflection device placed in the bore of said outer frame at said needle portion for directing the ultrasonic wave transmitted from said acoustic waveguide to said tissue under examination,
   wherein
   the acoustic waveguide has a distal portion with a diameter gradually increasing toward a distal tip end of the distal portion;
   the ultrasound beam deflection device comprises
      a first mirror (i) having a surface of a part of a paraboloid centered in the axial direction, (ii) placed around the acoustic waveguide so as to envelop the distal portion thereof, and (iii) facing to the distal end region of the needle portion; and
      a second mirror with a plane or curved surface that reflects the ultrasonic wave that has been reflected by the first mirror toward said tissue under examination.

2. The ultrasound probe according to claim 1, wherein said acoustic waveguide is housed in the bore of said outer frame and is attachable and/or removable from said needle portion along the axial direction.

3. The ultrasound probe according to claim 1, further comprising:
a hollow inner tube in said bore of said outer frame containing the needle portion and the extended portion,
wherein said inner tube is removable and repositionable against said needle portion within up to a limited distance along the axial direction, and
at least said acoustic waveguide and said ultrasound beam deflection device are housed within said inner tube.

4. The ultrasound probe according to claim 1, wherein said ultrasound beam deflection device is configured to focus an ultrasonic wave transmitted along said acoustic waveguide.

5. The ultrasound probe according to claim 1, further comprising acoustic windows for the transmission of an ultrasound beam directed by said ultrasound beam deflection device, wherein said acoustic windows are provided at a portion of said outer frame and are adapted to be in contact with said tissue under examination.

6. The ultrasound probe according to claim 1, wherein at least a part of said acoustic waveguide is made of sapphire or fused quartz.

7. The ultrasound probe according to claim 1, further comprising a higher mode of the Pochhammer-Chree wave is that is used as an ultrasonic wave.

8. The ultrasound probe according to claim 1, wherein at least a part of said acoustic waveguide is made of the material whose attenuation constant for an ultrasonic wave is substantially equal to or less than that of sapphire or fused quartz in the frequency range from 100 to 200 MHz.

9. The ultrasound probe according to claim 1, wherein the diameter of the portion adapted to be inserted into body tissue in said ultrasound probe is less than or equal to 1 mm.

10. An ultrasonograph using a needle-type ultrasound probe for insertion into body tissue, said ultrasonograph comprising:
said ultrasound probe according to claim 1; and
an ultrasound transmitting/receiving means,
wherein
an ultrasonic wave is transmittable via a surface of said acoustic waveguide and said ultrasound beam deflection device to the tissue under examination, and
the ultrasonic wave, reflected by the tissue and received via said ultrasound beam deflection device and via the surface of said acoustic waveguide, is separated and controlled.

11. An ultrasonograph using an ultrasound probe for insertion into body tissue, said ultrasonograph comprising:
said ultrasound probe according to claim 3;
a position-controlling means wherein the transmitting position of an ultrasound beam transmitted into the tissue from said ultrasound probe is controlled by moving the position of said acoustic waveguide within said region; and
an ultrasound transmitting/receiving means,
wherein
the ultrasonic wave is transmittable via a surface of said acoustic waveguide and via said ultrasound beam deflection device to the tissue under examination, and
the ultrasonic wave reflected from the tissue is received via said ultrasound beam deflection device and via the surface of said acoustic waveguide.

12. A method of ultrasonography using a diagnostic device according to claim 10, comprising the steps of:
inserting said ultrasound probe in or close to the tissue under examination;
transmitting an ultrasonic wave to said tissue under examination via a surface of said acoustic waveguide and via said ultrasound beam deflection device;
receiving the ultrasonic wave reflected from the tissue under examination via said ultrasound beam deflection device and via the surface of said acoustic waveguide; and
analyzing a reflected signal after separating the same from the transmitted signal in the received signal.

13. A method of ultrasonography using the ultrasonograph according to claim 11, comprising the steps of:
inserting said ultrasound probe in or close to the tissue under examination;
transmitting the ultrasonic wave to said tissue under examination via a surface of said acoustic waveguide and via said ultrasound beam deflection device;
receiving the ultrasonic wave reflected from said tissue under examination via said ultrasound beam deflection device and via the surface of said acoustic waveguide;
controlling the transmitting position of said ultrasound beam so as to scan said tissue under examination using said position-controlling means; and
analyzing a reflected signal after separating the same from the transmitted signal in the received signal.

14. The ultrasound probe according to claim 3, further comprising acoustic windows for the transmission of an ultrasound beam directed by said ultrasound beam deflection device,
wherein the acoustic windows are provided at a portion of said outer frame and said inner tube and are adapted to be in contact with said tissue under examination.

15. The ultrasound probe according to claim 1, wherein said ultrasound transducer is connected to a portion of said acoustic waveguide opposite to the distal portion by an acoustic medium which is made of the same material as that of said acoustic waveguide.

* * * * *